(12) United States Patent
Tajima et al.

(10) Patent No.: US 6,454,776 B1
(45) Date of Patent: Sep. 24, 2002

(54) SURGICAL OPERATING APPARATUS

(75) Inventors: Fujio Tajima, Tsuchiura; Kazutoshi Kan, Chiyoda; Yasuhiro Nemoto, Ogawa; Masakatsu Fujie, Ushiku, all of (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/520,721

(22) Filed: Mar. 8, 2000

(30) Foreign Application Priority Data

Jun. 21, 1999 (JP) ........................................... 11-173569

(51) Int. Cl.$^7$ ............................................... A61B 19/00
(52) U.S. Cl. ...................................................... 606/130
(58) Field of Search ..................... 606/130, 1; 700/302, 700/258, 250

(56) References Cited

U.S. PATENT DOCUMENTS 4,378,813 A * 4/1983 Feldstein et al.
5,755,725 A * 5/1998 Druais .......................... 606/130
5,971,976 A * 10/1999 Wang et al. ..................... 606/1
6,144,875 A * 11/2000 Schweikard et al. ......... 600/427

FOREIGN PATENT DOCUMENTS

JP            08299363         * 11/1996

* cited by examiner

Primary Examiner—Jeffrey A. Smith
(74) Attorney, Agent, or Firm—Antonelli, Terry, Stout & Kraus, LLP

(57) ABSTRACT

A surgical operating apparatus which reduces an adverse influence caused by a diseased portion of a patient while a surgical operation is carried out by the surgical operating apparatus. The surgical operating apparatus includes a disease portion tissue manipulator for treating a treating subject portion of the patient in response to an entered control command, a manipulation inputting unit for inputting a manipulation command to the disease portion manipulating means, and a detector for detecting a repeated movement of a diseased portion of said patient. The surgical operating apparatus adjusts the movement of the disease portion manipulator in response to the detection output from the detector.

7 Claims, 7 Drawing Sheets

SURGICAL OPERATING APPARATUS

BACKGROUND OF THE INVENTION

1. Field of the Invention

The present invention generally relates to a medical appliance. More specifically, the present invention is directed to a surgical operating apparatus for supporting medical treatments by surgical operators to disease portions in medical operations of circulatory organ systems, respiratory organ systems, brain/nerve systems, various organs located in abdominal cavities, and the like.

2. Description of the Related Art

Conventionally, as an apparatus for supporting an operation, the manipulator system for surgical operations is described in JP-A-8-299363.

The conventional technique disclosed in the above-explained JP-A-8-299363 is to provide such an operation supporting apparatus with low invasive characteristics. That is, when the surgical operation is carried out, the ultrasonic transducer elements are previously arranged on the body surface of the patient. While the surgical operation is executed, the image/measurement information of the disease portion of the patient are sequentially observed by employing the ultrasonic transducer elements, so that safety aspects of the patient can be secured. Conventionally, as image information, cardio echoes with using ultrasonic waves, fluorography and digital subtraction angiography (DSA) with using X-rays can be utilized. However, since diagnostic reading of cardio echo images would require expertise and further there is a limitation in the measurable tomographic direction, the echo imaging operation along a desirable diagnostic direction is not always allowed. Also, various sorts of image measuring apparatuses while using X-rays as modality own the following serious problem. That is, repeated radiation exposure problems occur, especially, unwanted large amounts of X-rays are exposed to doctors.

On the other hand, with respect to the circulatory organ system such as a heart and a blood vessel, since the shape of the heart is rapidly changed with a time elapse by the pulsation, this circulatory organ system is one of organ groups which can be very hardly treated in the surgical field. In a simple disease case, such a simple medical operating system is tried to be carried out by inserting a catheter in a meandering manner into femoral vessel. However, the medical operating system with using the catheter is limited only to such a simple medical case. As a consequence, in the medical case for requiring more complex treatments, while a body portion near a disease portion is largely incised, the medical operation is performed under such a condition that the pulsations of the heart are temporarily relaxed, reduced, or stopped by jointly using a jig for suppressing these pulsations and a heart-lung machine. This may give very heavy damages to the patient, may prolong the time required for the medical operation, may lower the success ratio of the medical operation and also the recovery degree after the medical operation, and furthermore, may prolong the recovery time. In order to reduce such a sort of damages, while the heart and lung stop is not essentially carried out and also the incised portion is made small, the medical operation must be completed within a short time duration. If the small incised portion is made while the medical operation is carried out, then the time duration required for carrying out the medical operation and also the recovery time can become very short. Also, QOL (quality of life) after the medical operation has been accomplished can be considerably improved, as described in the above-described JP-A-8-299369. However, in this case, an operating doctor himself must insert an operating tool from a small incised port into an interior portion of a patient, and must perform a medical operation within narrow space while paying his attention to movements of organs. Such a medical operation is a very difficult work even for an skilled operating doctor.

The present invention has been made to solve the above-described problems, and therefore, has an object to provide such a surgical operating apparatus capable of reducing an adverse influence given to a surgical operation without constraining a pulsation of a treating subject organ. This adverse influence is caused by such a fact that a disease portion is moved while a surgical operation is carried out.

SUMMARY OF THE INVENTION

To solve the above-described problems, while a treatment subject organ is moved, a medical process operation to this treatment subject organ is stopped and a surgical operating apparatus must be removed from this organ. To the contrary, while the treatment subject organ is under stationary state, the medical process operation with respect to this organ must be carried out. To this end, it is required to know when the treatment subject organ is moved, and also when this treatment subject organ is stopped. After recognizing when the treatment subject organ is moved and stopped, the following instruction may be issued to such an apparatus capable of performing either a physical process operation or a chemical process operation with respect to the treatment subject organ. That is to say, in response to a predicted movement of the treatment subject is stopped and the surgical operating apparatus is removed from this treatment subject organ, or the surgical operating apparatus is approached to the treatment subject organ so as to execute the process operation.

In other words, the above-described object may be achieved by such a surgical operating apparatus comprising: disease portion tissue manipulating means for treating a treating subject portion of a patient in response to an entered control command; manipulation inputting means capable of inputting a manipulation command to the disease portion manipulating means; and detecting means for detecting a condition of the patient; whereby: the surgical operating apparatus owns a function capable of adjusting the movement of the disease portion manipulating means in response to the detection output from the detecting means.

Also, the above-explained object may be achieved by such a surgical operating apparatus comprising: disease portion tissue manipulating means for treating a treating subject portion of a patient in response to an entered control command; manipulation inputting means capable of inputting a manipulation command to the disease portion manipulating means; and detecting means for detecting a condition of the patient; whereby: the surgical operating apparatus owns a function capable of adjusting a position of the disease portion manipulating means with respect to the treating subject portion in response to the detection output from the detecting means.

Also, the object of the present invention may be achieved by such a surgical operating apparatus: disease portion tissue manipulating means for treating a treating subject portion of a patient in response to an entered control command; manipulation inputting means capable of inputting a manipulation command to the disease portion manipulating means; detecting means for detecting a condition of the patient; and: adjusting means for outputting to the disease portion manipulating means, a command used to adjust the disease portion manipulating means so as not to be made in contact with the treating subject portion in response to the detecting output from the detecting means.

Furthermore, to achieve this object of the present invention, the detecting means detects a pulsation of the patient.

In addition, to achieve the above-described object of the present invention, the surgical operating apparatus is further comprised of: measuring means for measuring a movement of the treating subject portion; and said surgical operating apparatus owns a function capable of adjusting the movement of the disease portion manipulating means based upon stored data acquired from the output of the measuring means and the output of the detecting means.

BRIEF DESCRIPTION OF THE DRAWINGS

A better understanding of the present invention may be made by reading a detailed description with reference to the accompanying drawings, in which.

DETAILED DESCRIPTION OF THE EMBODIMENTS

Figure 1:
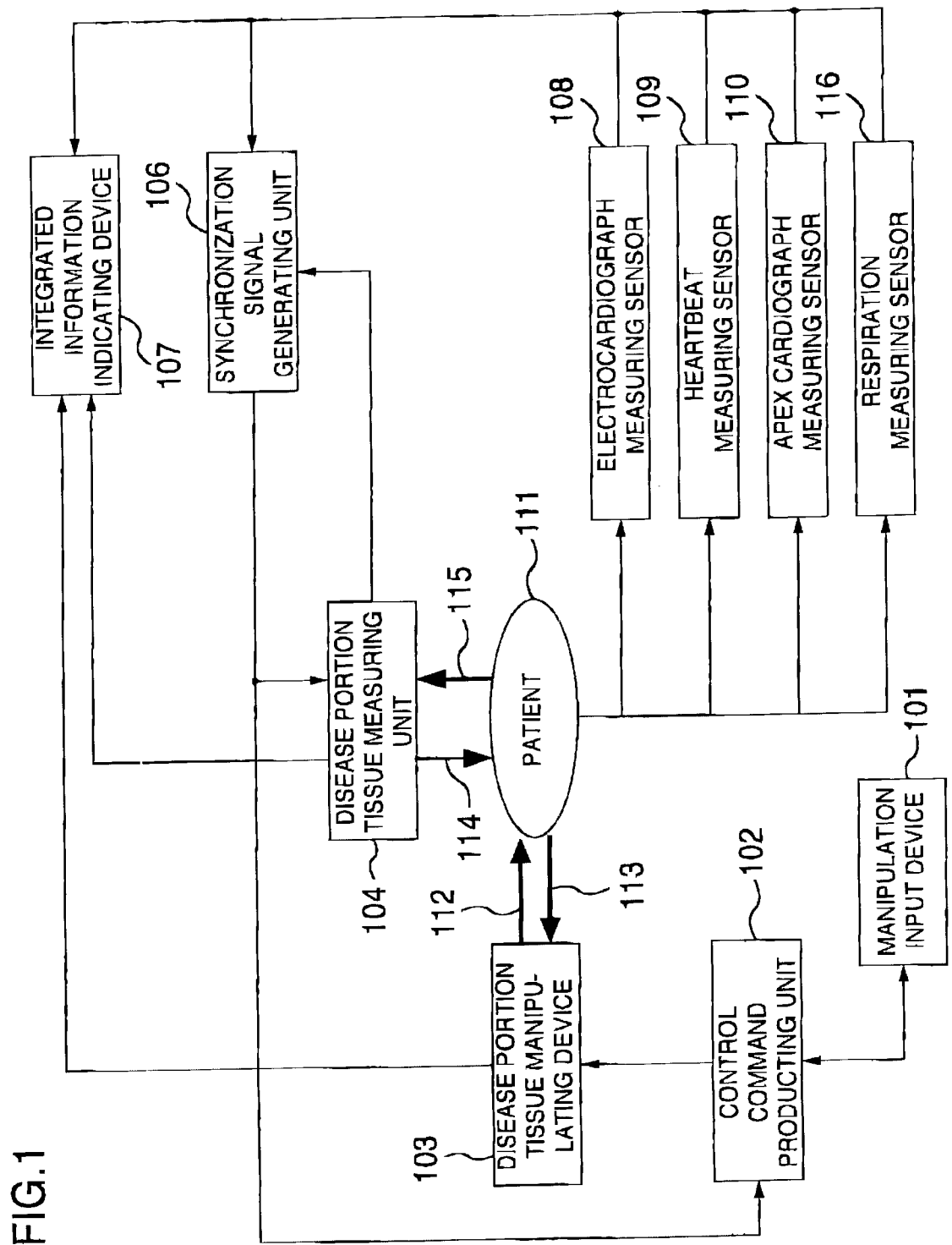
FIG. 1 is a systematic diagram for indicating a structural example of a surgical operating apparatus according to an embodiment mode of the present invention.

Referring now to drawings, a description is made of various embodiment modes of the present invention. FIG. 1 schematically indicates an arrangement of a surgical operating apparatus according to one preferred embodiment of the present invention. This surgical operating apparatus shown in FIG. 1 is arranged by employing an electrocardiograph measuring sensor 108 corresponding to an electrocardiograph measuring means for detecting a change in nerve potentials for emphasizing pulsations of a heart of a patient 111 who is treated by surgical operation; a heartbeat measuring sensor 109 corresponding to a heartbeat measuring means for detecting a heartbeat of the patient 111 who is similarly treated by the surgical operation; an apex cardiograph measuring sensor 110 corresponding to an apex cardiograph measuring means for detecting a pulsation of a heart of the patient 111 who is similarly treated by the surgical operation; and a respiration measuring sensor 116 corresponding to a respiration measuring means for detecting a respiration movement of the patient 111 who is similarly treated by the surgical operation. This surgical operating apparatus is further arranged by using a synchronization signal generating unit 106 corresponding to a synchronization signal generating means connected to the respective output terminals of the above-described electrocardiograph measuring sensor 108, the heartbeat measuring sensor 109, the apex cardiograph measuring sensor 110, and the respiration measuring sensor 116; an integrated information indicating device 107 corresponding to an integrated information indicating means; a disease portion tissue measuring unit 104 corresponding to a disease portion tissue measuring means connected to both the synchronization signal generating unit 106 and the integrated information indicating device 107; a control command producing unit 102 corresponding to a control command producing means connected to the output terminal of the synchronization signal producing unit 106; a manipulation input device 101 corresponding to a manipulation input means connected to the control command producing unit 102; and also a disease portion tissue manipulating device 103 corresponding to a disease portion tissue manipulating means connected to both the control command producing unit 102 and the integrated information indicating device 107.

It should be noted that arrow lines shown in this drawing indicate information and/or signals sent/received among the respective means. In particular, an arrow line 112 shows a manipulation from the disease portion manipulating device 103 to a disease portion; an arrow line 113 indicates various sorts of sensor information detected by the disease portion tissue manipulating device 103; an arrow line 114 represents various sorts of signals issued from the disease portion tissue measuring means 104 for measuring purposes; and also an arrow line 115 denotes a signal which is penetrated through a disease portion tissue, reflected from this disease portion tissue, or is reactively excited and radiated therefrom.

The electrocardiograph measuring sensor 108 senses a temporal change in electrocardio potentials of the patient 111. The heartbeat measuring sensor 109 senses a heartbeat of the patient 111. The apex cardiograph measuring sensor 110 mainly senses a heartbeat pulsation of the patient 111, namely senses mechanical motion thereof. The respiration measuring sensor 116 senses a respiration period of the patient 111. It should also be noted that the heartbeat measuring sensor 110 may be replaced by such an apparatus capable of measuring a blood pressure of a patient to output the measured blood pressure as an electric signal.

The disease portion tissue measuring unit 104 executes measurements (for example, MRI, X-ray CT, and ultrasonic echo) of treating organs by various modalities having low invasive characteristics before/after surgical operation is carried out. Then, the disease portion tissue measuring unit 104 acquires information of disease portion tissues within a short time period as mainly images, and supplies these image information to the integrated information indicating device 107 and the synchronization signal generating unit 106.

The synchronization signal generating unit 106 first performs a time sequential analysis before a surgical operation is carried out based upon the measurement information acquired from the disease portion tissue measuring unit 104, the electrocardiograph measuring sensor 108, the heartbeat measuring sensor 109, the apex cardiograph measuring sensor 110, and the respiration measuring sensor 116 so as to identify organ moving modes present in the subjective disease portion. Thus, this synchronization signal generating unit 106 studies an approximated pulsation period, an approximated respiration period, and timing among the respective information. While a surgical operation is carried out, the synchronization signal generating unit 106 sequentially and repeatedly studies these time periods and timing based upon the various information derived from the above-explained respective means, and further generates such a synchronization signal indicative of a pulsation period (involving pulsation and respiration in all of the below-mentioned cases) and a stationary period of the disease portion as a learning result. Then, the synchronization signal generating unit 106 supplies this generated synchronization signal to the above-explained control command producing unit 102.

The control command producing unit 102 produces a control command with respect to the disease portion tissue manipulating device 103 by combining the manipulation information entered from the manipulation input device 101 with the synchronization signal generated from the synchronization signal generating unit 106. Also, this control command producing unit 102 changes the control command in response to the values of the various sorts of sensor signals derived from the disease portion tissue manipulating device 103.

The disease portion tissue manipulating device 103 is operated in response to the control command entered from the control command generating unit 102, may change (for instance, surgical operation) the disease portion tissue in a physical manner, or a chemical manner by utilizing mechanical force, and radiation of various sorts of energy, and further transfers the sense signals derived from the various sorts of sensors mounted thereon to the control command producing unit 102.

The integrated information indicating device 107 properly integrates measurement information, modality-converted information, and time-sequential information to combine/arrange the above-explained information, and thus indicates the combined/arranged information as image information with speech to an operator. The measurement information is acquired from the disease portion tissue measuring unit 104 and mainly contains a tomographic image. The modality-converted information an endoscopic optical image and various sorts of sensor information of the disease portion tissue derived from the disease portion tissue manipulating device 103. The time sequential information is acquired from the electrocardiograph measuring sensors 108, the heartbeat measuring sensor 109, the apex cardiograph measuring sensor 110, and the respiration measuring sensor 116. It should also be noted that this integrated information indicating device 107 may be replaced by using the endoscopic image of the disease portion of interest, which is outputted from the endoscope.

The operator manipulates the manipulation input device 101 so as to actuate the disease portion tissue manipulating device 103 in the desirable manner, while referring to such information, i.e., mainly the image supplied from the integrated information indicating device 107, and inputs the desirable manipulation via the manipulation of the manipulation input device 101 to the disease portion tissue manipulating device 103. Both the disease portion tissue manipulating device 103 and the manipulation input device 101 constitute a master/slave manipulator in which while the manipulation input device 101 is used as a master, the disease portion tissue manipulating device 103 is operated as a slave via the control command producing device 102.

Figure 2:
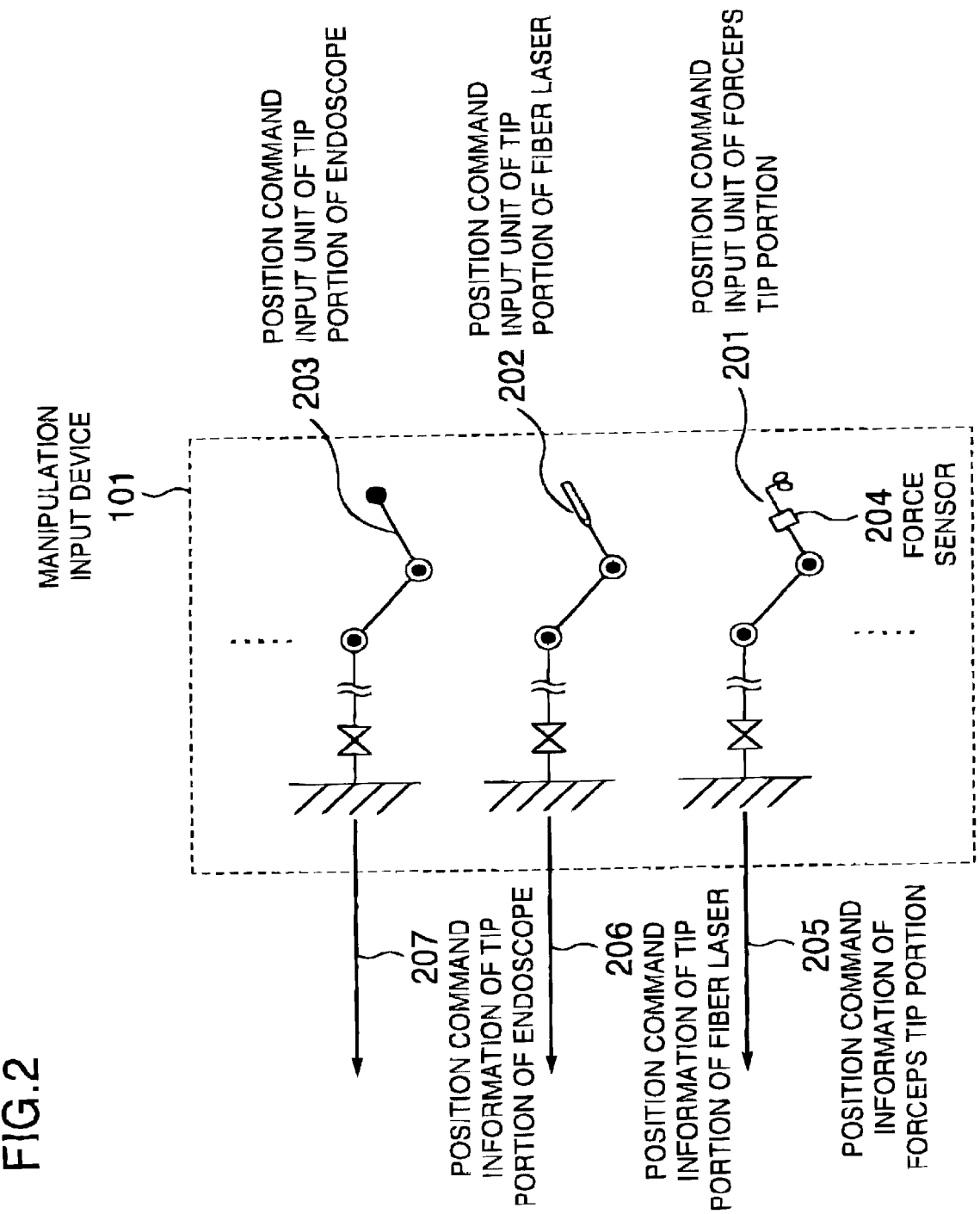
FIG. 2 is a conceptional diagram for representing an example of a manipulation input device shown in the surgical operating apparatus of FIG. 1.

Referring now to FIG. 2, the manipulation input device 101 will be explained. As indicated in this drawing, the operation input device 101 is arranged by containing a position/force command input unit 201 of a forceps tip portion; a position command input unit 202 of a fiber laser tip portion, and a position command input unit 203 of an endoscope tip portion. This manipulation input device 101 outputs position/force command information 205 of the forceps tip portion, position command information 206 of the fiber laser tip portion, and position command information 207 of the endoscope tip portion. The position/force command information 205 of the forceps tip portion, the position command information 206 of the fiber laser tip portion, and the position command information 207 of the endoscope tip portion constitute manipulation information.

A force sensor 204 is mounted on the position/force command input unit 201. As will be explained later, the forceps, the fiber laser, and the endoscope are mounted on a tip portion of a manipulator (slave) corresponding to an element of the disease portion tissue manipulating device 103. The respective command input units 201 to 203 (master of manipulator) command position, orientation/forces of these elements. It should be understood that since these elements are explained as one example, if other necessary instruments are provided, then input units for commanding position orientation/forces thereof are successively added. This idea is similarly applied to the manipulator (slave) of the disease portion tissue manipulating device 103.

The manipulation input device 101 corresponds to a plurality of articulated link mechanism, and outputs a position and orientation of a tip portion thereof and a force applied to this tip portion as a command value (manipulation information) of a manipulation input. As to the fiber laser and the endoscope, no force control is required. As to the forceps, since the force control is required while the contact operation is carried out, the position/force command input unit 201 is especially equipped with the force sensor 204 at the tip portion thereof.

The command information 205 to 207 outputted from the manipulation input device 101 are properly converted by the control command producing unit 102, and then the converted command information 205 to 207 is supplied as control commands of the manipulator which is one structural element of the disease portion tissue manipulating device 103. The contents of the converted command information will be explained later. The position/orientation of the tip portion of the manipulation input device 101 (tip portion of master manipulator) are obtained by substituting angles of the respective joints of the respective command input units 201 to 203, an angle sensed by a position sensor (not shown), or a value of a position for the forward kinetic formula related to this link mechanism. The force applied to the tip portion of the forceps is sensed by the force sensor 204. As previously explained, since the command information is applied while using the spatial coordinate of the tip portion of the manipulation input device 101 as a reference, the mechanical structures of the respective command input units 201 to 203 are not always made coincident with the respective manipulations of the disease portion tissue manipulating device 103.

Although not shown in the drawing, each of the joints provided in the respective command input units 201 to 203 is equipped with both an actuator and a joint locking mechanism. When the actuator is used to input a manipulation with respect to the manipulator (will be discussed later), this actuator may apply a reaction force in order that the operator enters the manipulation input in a smooth manner. The reaction force is a virtual force in the case that the manipulator may apply the manipulation response during the positional control operation. When the force control is carried out, this reaction force corresponds to a force reflection made from the manipulator. The joint locking mechanism is used so as to suppress the manipulation input action to the manipulator either in the pulsation period of the treatment subject point or the kinetic period thereof. The driving operation (namely, suppressing of manipulator action) of the locking mechanism and the releasing operation thereof are carried out in such a manner that the control command producing unit 102 which receives the synchronization signal sent from the synchronization signal generating unit 106 commands the manipulation input device 101 to be driven/released. It should also be noted that the manipulator shown in this drawing is one example, and any other mechanism constructions may be employed when such manipulator mechanisms may own a sufficient number of degree of freedom capable of inputting forces or positions/orientation with free degrees required for surgical operations, for example, the manipulators are arranged in serial/parallel manners, or serial-parallel combination manners. Also, although not shown in the drawings, the above-described mechanism is equipped with switches for locking/unlocking mechanism, and a manual switch for switching the control mode. These switching operations of the switches are performed by way of feet switches and/or speech controls.

The control command producing unit 102 combines the synchronization signal entered from the synchronization signal generating unit 106 with respect to the manipulation information inputted from the manipulation input device 101, and thus, produces a control command in such a way that the disease portion tissue manipulating device 103 is operated in accordance with the manipulation information entered from the manipulation input device 101 only during the stationary period of the organ to be treated. The control command producing unit 102 further produces a control command by which the locking operation of the link mechanism is instructed to the manipulation input device 101 so as to suppress the manipulation input during the time period other than the stationary period of the organ to be treated. Also, this control command producing unit 102 produces such a command that the manipulation reaction of the manipulation input device 101 is controlled in order that the transition from the stationary period to the pulsation (movement) period and the transition from the pulsation (movement) period to the stationary period can be performed in smooth manners (will be discussed later in detail).

Figure 3:
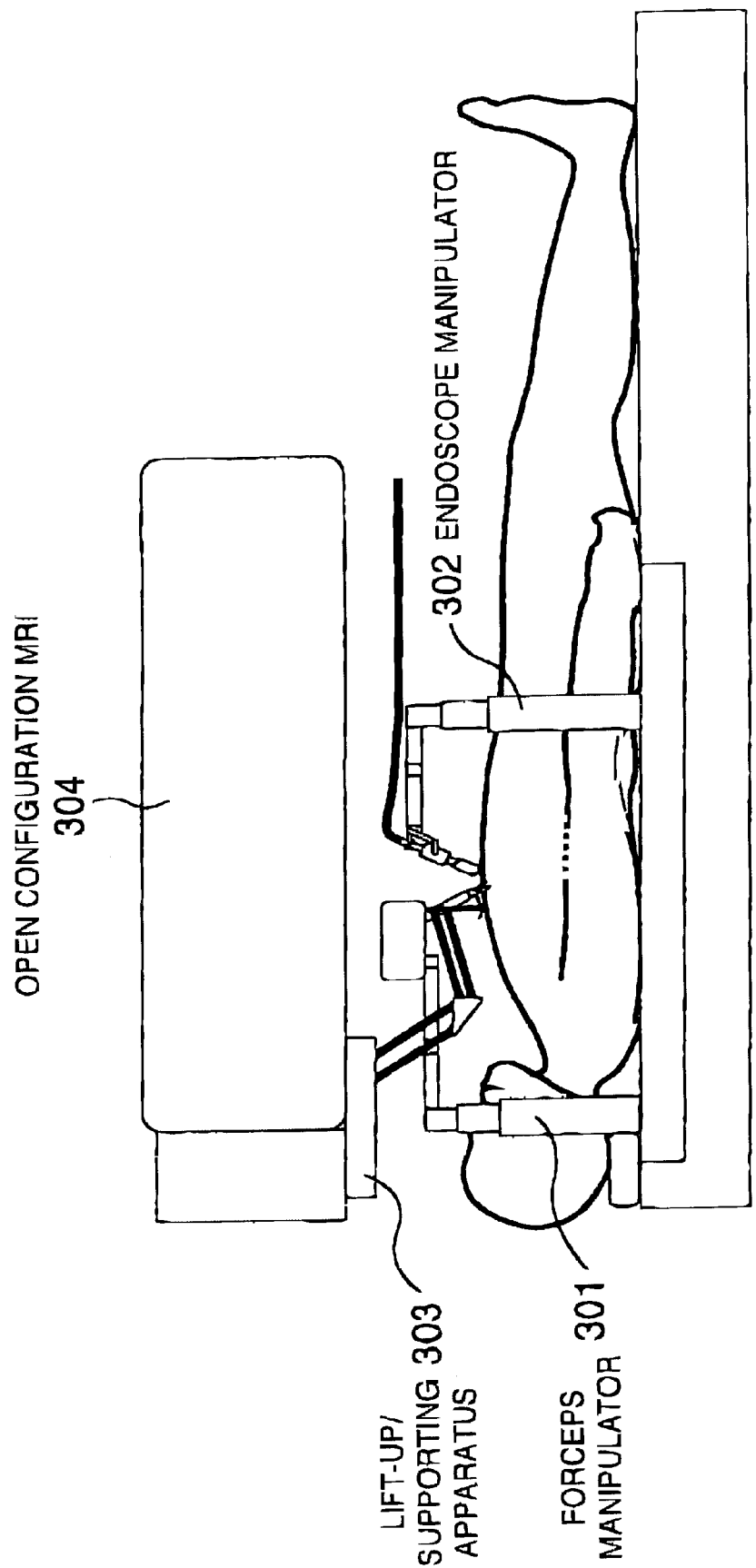
FIG. 3 is a sectional view for indicating an example of a disease portion tissue manipulator show in FIG. 1.

FIG. 3 illustratively shows an example of a structural arrangement of the disease tissue manipulating device 103. The disease portion tissue manipulating device 103 is constituted by a forceps manipulator 301, an endoscope manipulator 302, a lift-up/supporting apparatus 303, and an open configuration MRI 304. The magnet unit of this open configuration MRI 304 is represented. Either an operating tool or an endoscope is mounted on a tip portion of each of these manipulators. For the sake of an easing observation, only one set of manipulator is drawn in FIG. 3. A total number of manipulators may be changed in response to operating systems and conditions. As the operating tool, there are prepared: tools capable of producing mechanical forces such as a forceps and a knife; tools such as a fiber laser by which physical change/chemical change may occur at a subject point (subject disease portion) of an organ to be treated by radiating energy; and tools capable of conducting medicine to a subject point.

As shown in FIG. 1, the reactions to the disease portion by the mechanical forces and energy radiation are indicated by an arrow 112. As an example of the manipulator which constitutes the disease portion tissue manipulating device 103, an articulated link mechanism such as the forceps manipulator 301 may be employed. As previously described, this manipulator constitutes an articulated link mechanism equal to the manipulation input device 101, and a so-called "master/slave manipulator system". Both the forceps manipulator 301 and the endoscope manipulator 302, which correspond to the slave manipulator, solve the control command into a command of an angle, a position, or torque of each of these joints based upon the reverse kinetic formula. This control command is transferred from the manipulation input device 101 via the control command producing unit 102. This slave manipulator controls these joints to follow the angle, position, or torque command.

A proximity sensor (not shown) and a force sensor (not shown) are mounted on the tip portion of each of these manipulators (slave manipulators). The proximity sensor senses that the relevant manipulator is approached to the disease portion. The force sensor senses a contact force by the relevant manipulator. An arrow line 113 shown in FIG. 1 indicates sensor information of these sensors. The outer field sensor information (namely, information denoted by above arrow line 113) which is acquired by the interaction between these sensors and the disease portion, and the inner field sensor information such as the respective joint angles of the manipulators are sent from the disease portion tissue manipulating device 103 to the control command producing unit 102 so as to be used as such information for producing/changing the control command. The information related to the respective joint angles/contact forces and the proximity degrees is furthermore sent to the manipulation input device 101. This information is utilized so as to generate the force reflection and virtual reaction force which may suppress the manipulations which are deviated from the set range/set condition in the master mechanism.

On the other hand, the above-described information is also sent to the integrated information indicating device 107. This integrated information indicating device 107 performs such a process operation that the information related to the angle, the force, and the proximity distance is modality-converted so as to be expressed in the form of images and speech. It should be noted that since the structural members of the respective links of the disease portion tissue manipulating device 103 are expectively used under strong magnetic field, either a non-magnetic metal (aluminum, copper, titanium) or a polymer material (engineering plastics) is utilized. This treatment is similarly applied to the driving actuators for the respective joints, so that the below-mentioned actuators are used, namely, an actuator which does not produce electromagnetic force as a drive principle, and which does not use a magnetic metal as a material. For instance, an ultrasonic motor and a hydraulic/pneumatic actuator operated by water pressure and/or air pressure may be employed.

Alternatively, each of these joints may be driven by a polymer wire (namely, wire such as Kevlar made of polymer material having high strain strength characteristic), and an actuator for driving the polymer wire may be installed out of the magnetic field. Also, the lift-up/supporting apparatus 303 shown in FIG. 3 is one example of a lift-up/supporting apparatus. It should be understood that no driving actuator is mounted on the joint of this lift-up/supporting apparatus, but this lift-up/supporting apparatus is constructed of a mechanism capable of generating only resistance/holding forces (not shown). In other words, such a clutch as an electric viscosity fluid clutch is employed which utilizes the viscosity resistance force/holding force by the fluid cylinder, or the drive principle other than the electromagnetic force. As a result, the run away phenomenon of the lift-up/supporting apparatus caused by malfunction of the actuator can be essentially avoided.

Figure 4:
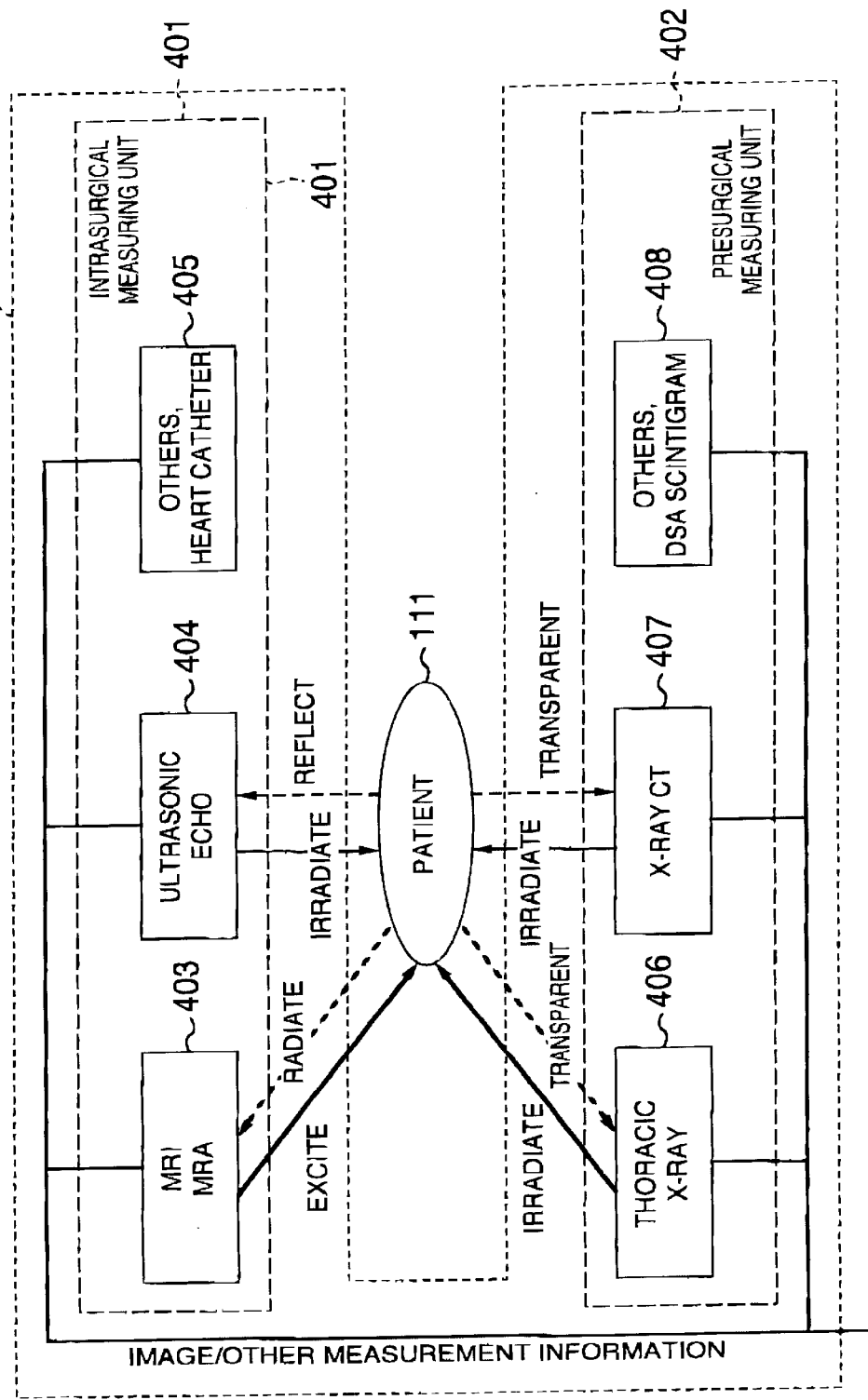
FIG. 4 is a conceptional drawing for indicating an example of a disease portion tissue measuring unit shown in FIG. 1.

Next, the disease portion tissue measuring unit 104 will now be explained with reference to FIG. 4. The disease portion tissue measuring unit 104 shown in this drawing is arranged by an inter-operation measuring unit 401 and a pre-operation measuring unit 402. The intrasurgical measuring unit 401 is arranged by an MRI apparatus 403, an ultrasonic echo imaging apparatus 404, and another intrasurgical measuring apparatus 405 such as heart catheter. The pre-operation measuring unit 402 is arranged by a thoracic X-ray imaging apparatus 406, and X-ray CT apparatus 407, and another pre-operation measuring apparatus 408 such as a DSA, scintigram, and magnetocardiograph and so on. As shown in this drawing, the disease portion tissue measuring unit 104 is constructed of plural modalities of measuring appliances.

An open configuration MRI is employed as the MRI apparatus 403 functioning as a main modality. An image indicating an arbitrary sectional plane of an organ to be treated is obtained by the MRI apparatus. Since the MRI apparatus may be used as an angiography, a blood flow may be visually observed by this MRI apparatus. The imaging operation by the MRI apparatus may be carried out not only before the surgical operation, but also during the surgical operation. Since the EPI (echo planer imaging) system and the FSE (fast spin echo) imaging system and so on are selected, the highspeed imaging operation can be carried out, so that the images can be updated within a short time period. While the surgical operation is carried out, the ultrasonic echo imaging apparatus 404 is jointly used. The information (images) measured from these apparatuses is sent to the integrated information indicating device 107. Also, before the surgical operation is carried out, various sorts of imaging operation are executed, for example, a blood vessel enhanced scintigraphic apparatus, the thoracic X-ray imaging apparatus 406, the X-ray CT apparatus 407, and the DSA. These images acquired before the surgical operation is carried out are previously supplied to the integrated information indicating device 107. While the surgical operation is carried out, these image are combined with the above-described images acquired during the surgical operation and thus, the combined images are indicated. It should be noted that solid arrow lines among arrow lines connected between the respective measuring apparatuses and the patient 111 correspond to the arrow line 114 shown in FIG. 1, and broken arrow lines correspond to the arrow line 115 shown in FIG. 1.

Figure 5:
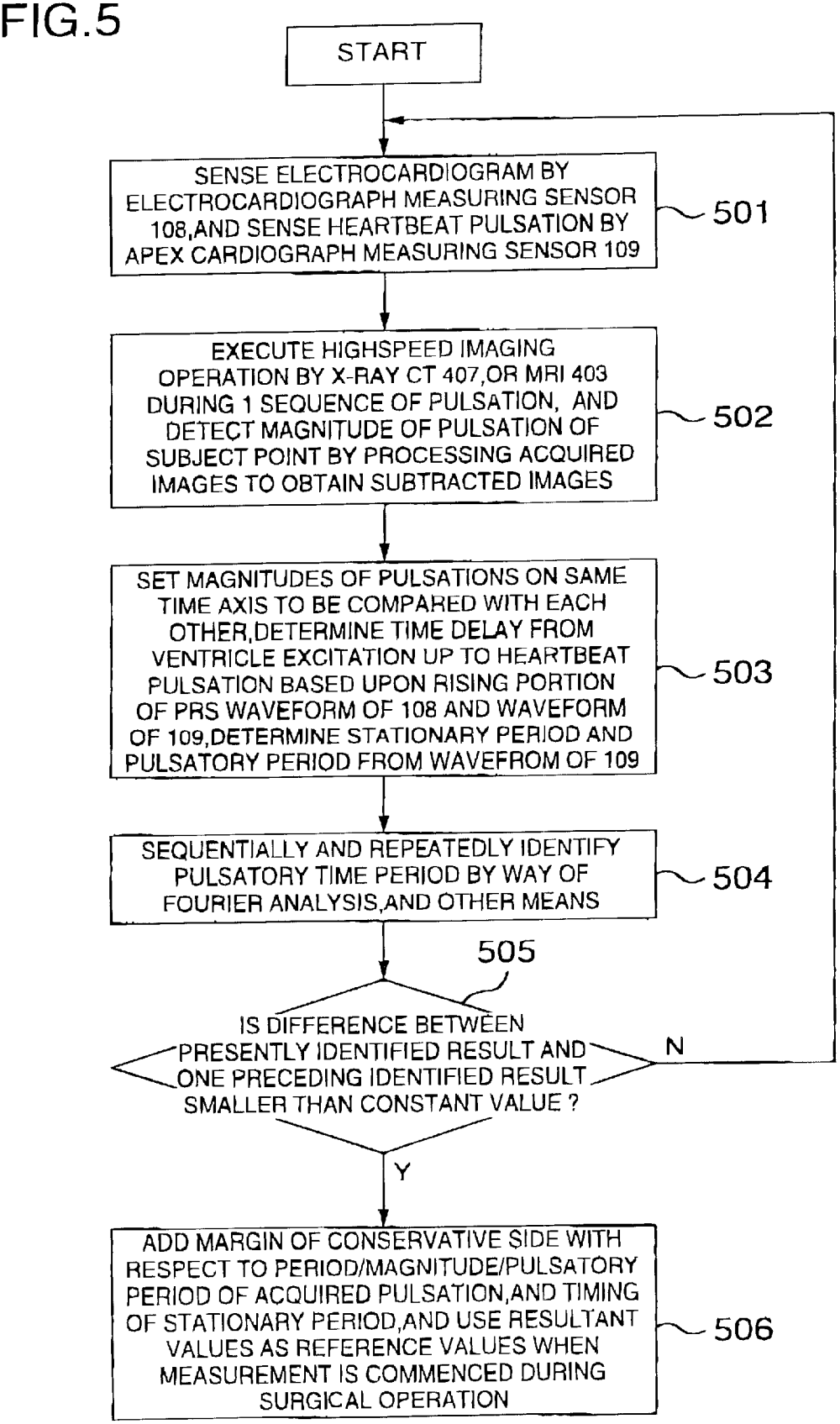
FIG. 5 is a flow chart for describing as example of sequential operation of a synchronization signal generating unit shown in FIG. 1.

Referring now to FIG. 5, a description will be made of a sequential operation of generating the synchronization signal by the synchronization signal generating unit 106. First, the electrocardiograph measuring sensor 108 senses an electrocardiograph, and the apex cardiograph measuring sensor 109 senses a heartbeat pulsation (step 501). At the same time, the highspeed imaging operation is carried out by actuating either the X-ray CT or the MRI within one sequence of a pulsation, and then the subtraction image processing operation is carried out to acquire a subtracted image (step 502). Thereafter, the subtracted images are compared with each other while being positioned on the same time axis. A time delay defined from a ventricle excitation to a heartbeat pulsation can be measured from a rising edge of a PRS waveform of an electrocardiograph (will be referred to as an "ECG" hereinafter) and a waveform of an apex cardiograph (will be referred to as an "ACG" hereinafter). Based upon the waveform of the ACG, both a pulsation period and a stationary period can be determined. Also, at this time, a magnitude of a pulsation is obtained from the above-described image subtraction (step 503). Since this process operation is repeatedly carried out, both the time delay defined from the ventricle excitation to the heartbeat pulsation and also the magnitude of the pulsation at this time can be studied.

Furthermore, a time period itself of a pulsation is acquired by repeatedly identifying time sequential signals of the ECG and the ACG with employment of the Fourier analysis, or the auto regressive moving average (ARMA) model (step 504). The measurement and the identification learning are repeatedly carried out until a difference between the present identified result and the identified result obtained one previous identifying operation becomes smaller than, or equal to a predetermined value at a step 505. For instance, a square summation is calculated for a difference between coefficients of a model, and then this square summation is compared with a certain threshold value. Then, margins for conservative side are added to the time period of the pulsation, the magnitude thereof, the pulsatory period thereof, the time of the stationary period, and further the transition timing, which have been acquired before the surgical operation is carried out. The resultant values are used as reference values when the measurement operation is commenced while the surgical operation is carried out (step 506).

While the surgical operation is performed, the above-explained reference values are used as initial values, and the learning is sequentially repeated in a similar manner that before the surgical operation is carried out. Thus, the respective calculated values are updated/corrected. As a result, the time period of the pulsation, the magnitude thereof, the time of both the pulsatory period and the stationary period, and also the transition timing can be predicted immediately before the surgical operation is carried out. However, these values are predicted values, and if the transition timing (especially, transition timing from stationary period to pulsatory period) is erroneously detected, then a very risky case will occur. Therefore, a change in the signals used to indicate a transition from a stationary period to a pulsatory period may occur on the conservative side, namely may occur in a earlier stage; the earlier one between the predicted timing and the rising edge of the PRS waveform of the actual ECG waveform. Similarly, a change in the signals used to indicate a transition from a pulsatory period to a stationary period may occur on the conservative side, namely may occur in a later stage; the latter one between the predicted timing and a time instant when an inclination of the actual ACG waveform is smaller than, or equal to a certain constant value, and the value itself is smaller than, equal to a constant value.

Figure 6:
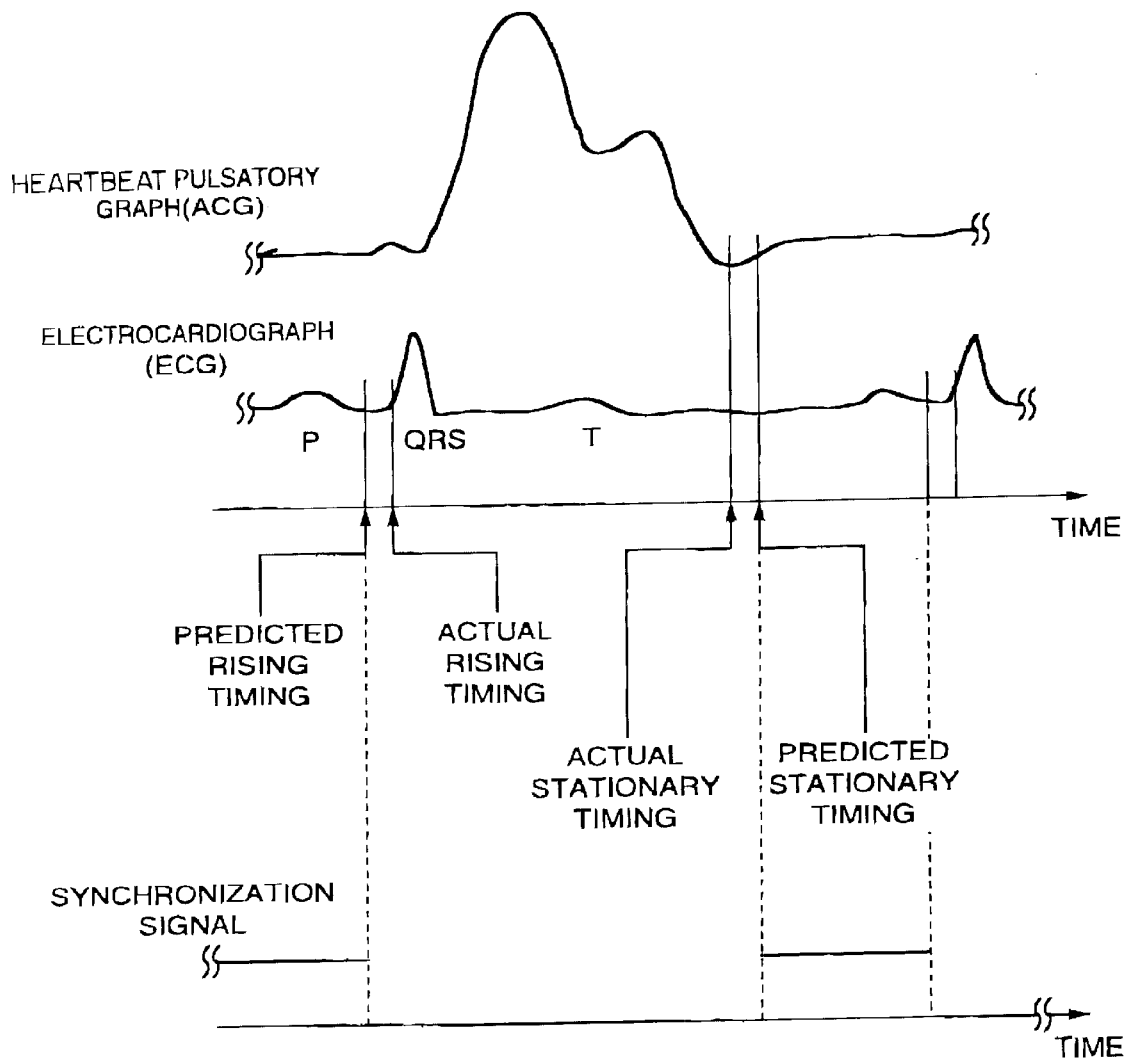
FIG. 6 is a time chart for representing an example of such a case that transition timing from a predicted pulsatory period to a stationary period, and also another transition timing opposite to this transition timing are present on a safety side.

FIG. 6 shows an example of such a case that predicted transition timing is present on the conservative side. In other words, FIG. 6 indicates typical timing of apex-cardiograph/electrocardiograph waveforms. For instance, as shown in this drawing, a synchronization signal is conceivable as follows. A level of this synchronization signal becomes a Low (zero) during a transition from a stationary period to a pulsation period, and becomes a High (certain constant level) at a time instant when the pulsation period is transferred to the stationary period. Practically speaking, in a case of a heart, for example, a length of a pulsation period is on the order of 0.5 seconds. In response to rising/falling edges of this signal, the control operations are performed with respect to sending operation (execution of surgical operation)/suppressing operation (stationary/saving movements) of control commands to the disease portion tissue manipulating device 103 of the control command producing unit 102, and also the operation suppression/release actions of the manipulation input device 101.

There are some cases that the respiration movements may give adverse influences, or may mainly change the sensor measurement results, depending upon the body portions to be treated. In this case, the respiration measuring sensor 116 is additionally provided with the above-explained sensor groups. Then, after the respiration sensor output is added to the relevant sensor output, the synchronization signal generating unit 106 studies the added sensor output to thereby output such a synchronization signal indicative of a motion period and a stationary period for combining a pulsation and a respiration movement. Upon receipt of this synchronization signal, the control command producing unit 102 commands the execution/suppression (stationary/avoidance movements) of the surgical operation by the disease portion tissue manipulating device 103, and the suppressing/releasing operation of the manipulation input operation of the manipulation input device 101. In other words, while the level of the synchronization signal is a Low (namely, pulsation period), this control command producing unit 102 issues such a command that the mechanical unit of the manipulation input device 101 is locked (namely, is fixed not to be moved). Also, this control command producing unit 102 issues such an instruction that the command values for the positions and the like with respective to the respective mechanisms employed in the disease portion tissue manipulating device 103 are kept constant (in case that stationary state is instructed), or the distance between the distal end of the disease portion tissue manipulating device 103 and the surface of the disease portion is kept constant. While the level of the synchronization signal becomes a High, the control command producing unit 102 limits the command value of the manipulation information in order that the command value does not exceed the limitation of the manipulation information entered from the manipulation input device 101 namely, a preset variable range of motion and the upper limit values of the velocity/ acceleration, and then sends the control command to the disease portion tissue manipulating device 103. On the other hand, in such a case that the command value of the manipulation information exceeds the set limit values, the reaction force is increased so as to increase the hand reaction force, so that the user never inputs excessive manipulation values.

Figure 7:
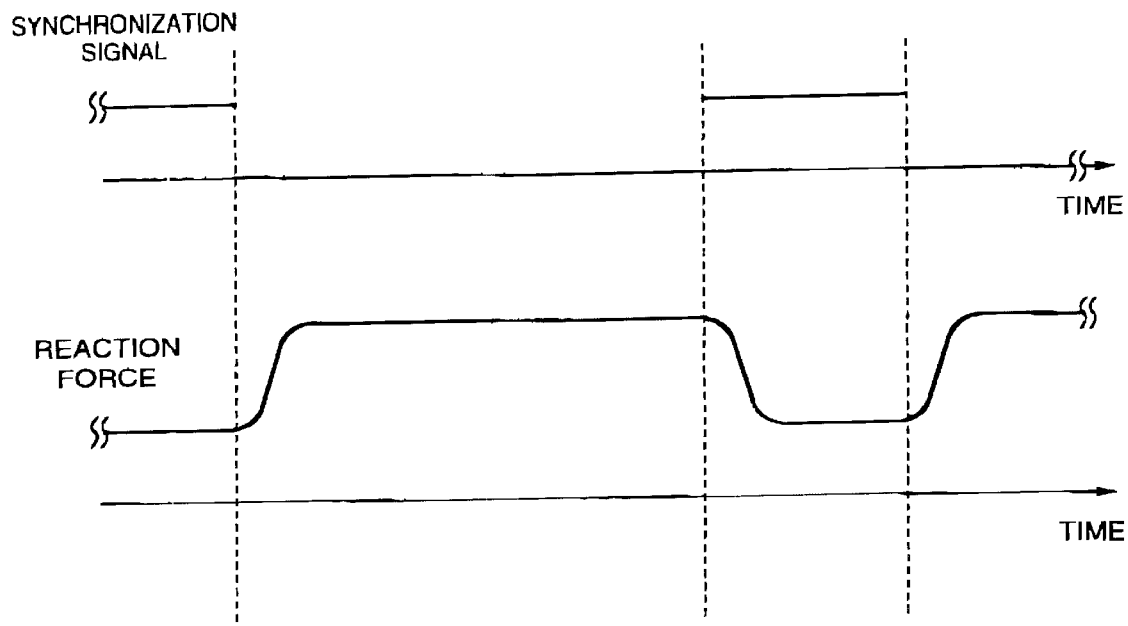
FIG. 7 is a time chart for representing an example of a temporal change in manipulation reactive force exerted by the manipulation input device employed in the surgical operating apparatus according to the embodiment mode shown in FIG. 1.

For example, a temporal change in reaction forces occurs as indicated in FIG. 7. When the state is transferred from a Low to a High, if locking of the mechanism unit of the manipulation input device 101 is rapidly released and this condition is maintained, then the hand reaction force given to the user rapidly becomes light, so that the user may mistakenly enter such an excessively large manipulation input against his/her will. To avoid such a problem, while the reaction force is set to a large value just after locking of the mechanism unit of the manipulation input device 101 is released, the produced reaction force is controlled in order that this reaction force is gradually and smoothly reduced. Conversely, when the state is transferred from a High to a Low, the mechanism unit of the manipulation input device 101 is rapidly locked. If this mechanism locking phenomenon is maintained, then the user may mistakenly enter such an excessively large manipulation input against his/her will.

As a result, there is a probability that the hand of this user who manipulates this manipulation input device 101 is injured. As a consequence, the generated reaction force is controlled in such a manner that the reaction force is gradually and smoothly increased immediately before the mechanism unit of the manipulation input device 101 is locked (namely, pulsation time instant during next time period is predicted by repetitive learning, and is sensed based upon PRS waveform). In this drawing, a change in the reaction forces is presented by such a way that this reaction force change starts from the falling edge timing of the synchronization signal, and then reaches such a magnitude by which the user cannot simply move this mechanism until the heartbeat pulsation is commenced. Alternatively, this change in the reaction forces may be commenced from, for instance, timing located far from the predicted transition timing. Also, the change in the reaction forces is set in such a manner that this reaction force change occurs at a sufficiently fast time constant in order that the reaction force change is settled until the rising time of the heartbeat pulsation.

Although the above-explained system may be realized by only employing the reaction force generating unit, the locking mechanism unit is required in order to maintain safety performance. This locking mechanism unit is capable of preventing the overload of the reaction force generating unit, and also is capable of firmly suppressing the manipulation input. It should also be noted that even when the position/orientation input is made while the manipulation input device 101 is locked in the pulsation period, the control command producing unit 102 holds the command value issued just before the transition occurs, for example, the position/orientation.

Figure 8:
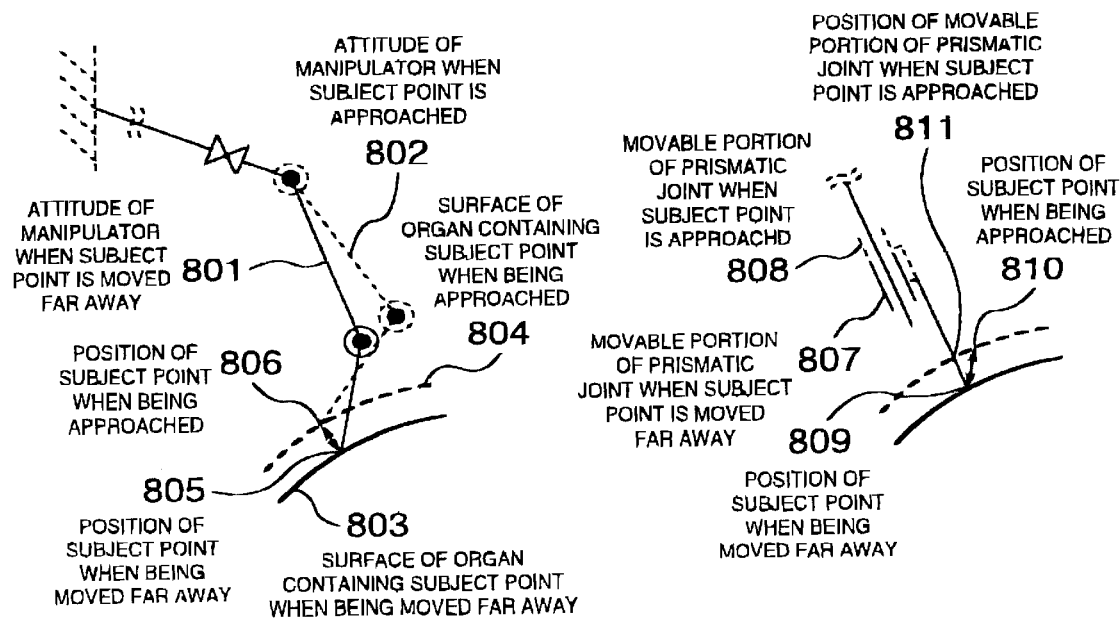
FIG. 8 is a conceptional diagram for indicating an example of movement of organs containing a subject point and also an example of movement of a manipulator used for these organs in the surgical operating apparatus shown in FIG. 1.

In the stationary period, the disease portion tissue manipulating device 103 may follow the input derived from the manipulation input device 101. In the pulsation period, this disease portion tissue manipulating device 103 automatically performs the avoidance movement in response to the control command entered from the control command producing means in order that the manipulator does not collide with the subject disease organ which moves in a pulsatory manner. A first consideration is made of such a case that the treating point is a surface of an organ. FIG. 8 schematically indicates a movement of an organ containing a subject point and a movement of the manipulator with respect to this movement. In FIG. 8, a solid line 801 indicates an attitude of the manipulator in the case that the subject point is moved far away from this manipulator; a dotted line 802 shows an attitude of the manipulator in the case that the subject point is approached to this manipulator; and a solid line 803 represents a surface of an organ involving the subject treatment point when the organ is moved far away from the manipulator. Also, a solid line 804 represents a surface of an organ involving a subject point in such a case that the organ is approached to the disease portion tissue manipulating device 103; a position 805 shows a position when a subject treatment point is moved far away; a position 806 indicates a position when a subject treatment point is approached; a solid line 807 shows a variable portion of a prismatic joint when a subject point is moved far away; a dotted line 808 shows a variable portion of a prismatic joint when a subject point is approached; a position 809 is a position of a subject treatment point when the organ device 103 is moved far away therefrom; a position 810 is a position of a subject treatment point when the organ is approached; and a position 811 represents a tip position of a variable portion of a prismatic joint when a subject treatment point is approached.

Roughly speaking, a movement (magnitude and direction) of a subject treatment point in a pulsation period may be identified by executing repetition learning before/during a surgical operation is carried out. Based upon this identified movement of the subject treatment point, a pulsation time instant during next time period, and a move distance/direction at the subject point may be predicted. These values are applied as target values for the avoidance movement of the tip portion of the manipulator. The avoidance movement of the manipulator is commenced just before the predicted pulsation time instant of the next time period in order to avoid a collision between this manipulator and the subject point, which is caused by the pulsation of this subject point. The tip portion of the manipulator performs the avoidance movement in correspondence with a single pulsation sequence, and then this tip portion is returned to the position/orientation of this manipulator just before this avoidance movement is started at the end of the pulsation period.

It should be noted that the prediction value obtained from the learning operation is applied to a stable medical case as to the pulsation period. In the case of such a medical case in combination with a symptom such as an irregular pulse (arrhythmia) and ventricular preexcitation, since there is a limitation in predicting of movements by the learning operation, a user introduces the actually-sensed timing of the rising/falling edges of the electrocardiograph/apex cardiograph with a top priority.

The movement required for the tip portion of the manipulator to avoid the organ may be carried out in such a manner that while the necessary movement of this tip portion is soled by way of the inverse kinematics to be resolved to movements of the respective joints, the movement is performed along the predicted motion direction of the subject point by moving the respective joints. This method is simply illustrated in a left side of FIG. 8. Although not shown in this drawing, it is assumed that the manipulator owns sufficient degree of freedom required to execute both the avoidance movement and the necessary work. In other words, there are some possibilities that the degrees of freedom of the manipulator is selected to be larger than, or equal to 1. In this case, both the movement of the subject point and the movement of the tip portion of this manipulator are made coincident with the subject treatment point at the solid line 803 and the position 806, or maintain the same constant distance. Alternatively, while a joint of a topmost tip portion of the manipulator is constituted by a prismatic joint, only this joint may be moved down along a immediately backward direction with respect to the approaching direction when the avoidance movement is carried out. This condition is simply illustrated on a right side of FIG. 8. In the drawing, only the prismatic joint is illustrated which correspond to the topmost tip joints. In such a case, when the subject point is moved far away from the manipulator, the position of this subject point is made coincident with the position of the tip portion of the manipulator at the position 809, or maintains a constant. However, when the subject point is approached to the manipulator, the positional relationship between the position 811 of the tip portion of the manipulator and the position 810 of the subject point is not made coincident with the positional relationship thereof when the subject point is moved. However, it would be enough for the manipulator to be moved down over a sufficient distance along the immediate backward direction in order that the manipulator is not made in contact with the approached organ.

However, this case may be merely applied to the trajectory, but a sudden movement irrespect to the past historical relationship may occur. As a result, different from the previous case, a sensor for measuring a distance between this sensor and a subject treatment point is mounted on the tip portion of the manipulator, and then such an avoidance movement is carried out in such a manner that the tip portion of this manipulator always keeps a distance longer than, or equal to a constant distance with respect to the subject treatment point in the pulsation period. As this sensor, the following sensor structures may be conceived. That is, a sensor is made by combining a light emitting diode (LED) and a phototransistor. Also, a so-called "wisker sensor" may be employed which senses a movement and a bent portion of a narrowed flexible antenna at a root portion thereof. As the sensing method at the root portion, there are one sensing method for sensing distortion of the antenna by way of a strain guage, and another sensing method for measuring a strength of reflection light varied in response to a bending degree can be considered by using an optical fiber and making light pass through the optical fiber. Alternatively, an optical localizing device may be employed as this sensor. This optical localizing device is constituted by utilizing reflections of ultrasonic waves, a light emitting unit, a CCD camera, and the like. Alternatively, in the case of a contact work, a distance becomes zero. In such a contact work case, the movement of the tip portion of the manipulator is controlled in such a manner that a contact force of the tip portion of the manipulator is kept lower than, or equal to a constant force.

When the subject treatment point is an interior portion of an organ, while an incised portion is recognized as a surface, the avoidance motion of the tip portion of the manipulator is carried out in the same sequential operation as the above case. In such a surgical operation case that a certain operation tool is inserted from a small incised portion into an interior portion of an organ, another manipulation means (for instance, compact articulated manipulator, or active catheter) is mounted on the tip portion of the manipulator, and thus, this manipulation means is inserted from a very small incised portion thereinto. In the latter case, the following control operation is carried out. That is, while a follow/avoidance movement of the manipulator is repeatedly carried out in order that the manipulator may keep a zero distance with respect to the insertion point of the organ surface, the compact manipulator inserted into the interior portion executes the positional control operation in the stationary period, and also executes the avoidance movement, or a so-called "compliance control" in the pulsation period. A total number of joints employed in this compact manipulator is relatively increased, and these joints are arranged in a redundant manner. As a consequence, even when the capacity of the interior portion of the organ is narrowed due to pulsation and/or respiration, this compact manipulator may be configured without injuring the inner wall. When the catheter is employed, the follow/avoidance movement is carried out with respect to the surface. Since the catheter contained, compliance in view of a material aspect, no specific control operation is required for this catheter when being inserted into the interior portion of the organ.

Since the surgical operating apparatus is constituted by employing the above-described arrangement, the user can continuously carry out the medical treatment without paying his attention to the movements of the subject disease portion caused by the pulsation/respiration movements.

As previously explained in detail, in accordance with the surgical operating apparatus of the present invention, while this surgical operating apparatus detects the moving state of the disease organ to be treated, which is caused by the pulsation and the respiration thereof, the manipulation input and also the disease portion tissue manipulation are intermittently suppressed in response to the signal capable of identifying this detected moving state. As a consequence, this surgical operating apparatus can reduce such an adverse influence given to the surgical operation, which is caused by the movement of the disease portion while the surgical operation is carried out.

What is claimed is:

1. A surgical operating apparatus comprising;

disease portion tissue contact manipulating means for contact treating a treating subject portion of a patient in response to an entered control command;

manipulation inputting means capable of inputting a manipulation command to said disease portion contact manipulating means; and means for detecting a repeated movement of a diseased portion of said patient, for determining a movable period and a stationary period, and for providing a detection output indicative thereof; whereby:

said surgical operating apparatus adjusts the movement of said disease portion contact manipulating means in contact with the treating subject portion of the patient in response to the detection output from said detecting means indicating the stationary period.

2. A surgical operating apparatus comprising;

disease portion tissue contact manipulating means for contact treating a treating subject portion of a patient in response to an entered control command;

manipulation inputting means capable of inputting a manipulation command to said disease portion contact manipulating means; and means for detecting a repeated movement of a diseased portion of said patient, for determining a movable period and a stationary period, and for providing a detection output indicative thereof; whereby:

said surgical operating apparatus adjusts a position of said disease portion contact manipulating means with respect to said treating subject portion in response to the detection output from said detecting means indicating both the movable period and the stationary period.

3. A surgical operating apparatus comprising:

disease portion tissue contact manipulating means for contact treating a treating subject portion of a patient in response to an entered control command;

manipulation inputting means capable of inputting a manipulation command to said disease portion contact manipulating means;

means for detecting a repeated movement of a diseased portion of said patient, for determining a movable period and a stationary period, and for providing a detection output indicative thereof; and:

adjusting means for outputting to said disease portion contact manipulating means, a command used to adjust said disease portion contact manipulating means so as not to be made in contact with said treating subject portion in response to the detecting output from said detecting means indicating a movable period.

4. A surgical operating apparatus as claimed in any one of the preceding claims 1 to 3 wherein:

said detecting means detects a pulsation of the diseased portion of said patient.

5. A surgical operating apparatus as claimed in any one of the preceding claims 1 to 3 wherein:

said surgical operating apparatus is further comprised of:

measuring means for measuring a movement of said treating subject portion; and said surgical operating apparatus adjusts the movement of said disease portion manipulating means based upon stored data acquired from the output of said measuring means and the output of said detecting means.

6. A surgical operating apparatus as claimed in any one of the preceding claims 1–3, wherein said detecting means in detecting the repeated movement of the diseased portion of the patient detects repeated nonmovement of the diseased portion of said patient as the stationary period, and said surgical operating apparatus adjusts the movement of said disease portion contact manipulating means in contact with the treating subject portion to occur at least during the stationary period of nonmovement of the diseased portion of said patient as detected by said detecting means.

7. A surgical apparatus according to claim 6, wherein said surgical operating apparatus suppresses contact of said disease portion manipulating means with the diseased portion of said patient during the movable period of movement of the diseased portion of said patient as detected by said detecting means.

* * * * *